US00RE48899E

(19) United States
(12) Reissued Patent
Kliner et al.

(10) Patent Number: US RE48,899 E
(45) Date of Reissued Patent: Jan. 25, 2022

(54) SLANTED FBG FOR SRS SUPPRESSION

(71) Applicant: nLIGHT, Inc., Vancouver, WA (US)

(72) Inventors: Dahv A. V. Kliner, Portland, OR (US); Timothy S. McComb, Portland, OR (US)

(73) Assignee: nLIGHT, Inc., Camas, WA (US)

(21) Appl. No.: 16/395,057

(22) Filed: Apr. 25, 2019

Related U.S. Patent Documents

Reissue of:
(64) Patent No.: 9,634,462
Issued: Apr. 25, 2017
Appl. No.: 14/884,642
Filed: Oct. 15, 2015

U.S. Applications:
(60) Provisional application No. 62/064,371, filed on Oct. 15, 2014.

(51) Int. Cl.

| | |
|---|---|
| ***H01S 3/067*** | (2006.01) |
| ***G02B 6/02*** | (2006.01) |
| ***H01S 3/30*** | (2006.01) |
| ***G02B 6/25*** | (2006.01) |
| ***C07K 14/705*** | (2006.01) |
| *A61K 38/00* | (2006.01) |

(52) U.S. Cl.
CPC ..... *C07K 14/705* (2013.01); *A61K 38/00* (2013.01); *C07K 2319/02* (2013.01); *C07K 2319/30* (2013.01)

(58) Field of Classification Search
CPC .. H01S 3/302; H01S 3/06708; H01S 3/06754; H01S 3/0675; H01S 3/0078; H01S 2301/02; G02B 6/02085; G02B 6/25
See application file for complete search history.

(56) References Cited

U.S. PATENT DOCUMENTS

| | | | | |
|---|---|---|---|---|
| 4,130,343 | A | 12/1978 | Miller et al. | |
| 5,620,495 | A * | 4/1997 | Aspell | G02B 6/02142 65/392 |
| 5,671,307 | A * | 9/1997 | Lauzon | G02B 6/02085 385/10 |
| 6,132,104 | A | 10/2000 | Bliss et al. | |
| 6,265,710 | B1 | 7/2001 | Walter | |
| 6,434,177 | B1 | 8/2002 | Jürgensen | |

(Continued)

OTHER PUBLICATIONS

Wu, Meng-Chou. Pressure Effects on the Temperature Sensitivity of Fiber Bragg Gratings. NASA Langley Research Center. (Year: 2013).*

(Continued)

*Primary Examiner* — Deandra M Hughes
(74) *Attorney, Agent, or Firm* — Klarquist Sparkman, LLP

(57) ABSTRACT

An example apparatus includes an optical fiber including a core and cladding, the core being situated to propagate an optical beam along a propagation axis associated with the core, and at least one fiber Bragg grating (FBG) situated in the core of the optical fiber, the fiber Bragg grating including a plurality of periodically spaced grating portions situated with respect to the propagation axis so that light associated with Raman scattering is directed out of the core so as to reduce the generation of optical gain associated with stimulated Raman scattering (SRS).

28 Claims, 4 Drawing Sheets

(56) References Cited

U.S. PATENT DOCUMENTS 6,528,239 B1 * 3/2003 Starodubov ..... G02B 6/02104 430/290
6,556,340 B1 4/2003 Wysocki et al.
6,801,550 B1 10/2004 Snell et al.
6,839,163 B1 1/2005 Jakobson et al.
6,980,578 B2 * 12/2005 Ramachandran .. G02B 6/02095 372/102
7,079,566 B2 7/2006 Kido et al.
7,170,913 B2 1/2007 Araujo et al.
7,235,150 B2 6/2007 Bischel et al.
7,373,070 B2 5/2008 Wetter et al.
7,389,022 B2 6/2008 De Barros et al.
7,590,155 B2 * 9/2009 Liu ..... H01S 3/06708 372/18
7,748,913 B2 7/2010 Oba
7,764,723 B2 7/2010 Ovtchinnikov et al.
7,839,901 B2 11/2010 Meleshkevich et al.
7,883,535 B2 2/2011 Cantin et al.
8,027,555 B1 9/2011 Kliner et al.
8,317,413 B2 11/2012 Fisher et al.
8,433,161 B2 4/2013 Langseth et al.
8,441,718 B2 * 5/2013 Mead ..... H01S 3/0675 359/326
8,537,871 B2 9/2013 Saracco
8,542,971 B2 9/2013 Chatigny
8,693,824 B2 4/2014 Hu
8,718,430 B2 5/2014 Chatigny
8,774,237 B2 7/2014 Maryashin et al.
9,014,220 B2 4/2015 Minelly et al.
9,056,710 B1 * 6/2015 Strickland ..... B65D 88/123
9,293,889 B1 * 3/2016 Henry ..... H01S 3/0675
9,634,462 B2 4/2017 Kliner et al.
2002/0097963 A1 7/2002 Ukechi et al.
2002/0139151 A1 * 10/2002 Davis ..... C03B 37/01869 65/419
2003/0063629 A1 * 4/2003 Davis ..... H01S 3/063 372/6
2004/0056183 A1 * 3/2004 Eggleton ..... G02B 6/124 250/227.23
2005/0063430 A1 * 3/2005 Doucet ..... H01S 3/0675 372/23
2005/0220403 A1 * 10/2005 Dykaar ..... G02B 6/4214 385/31
2006/0029111 A1 * 2/2006 Liu ..... H01S 3/06708 372/6
2007/0177642 A1 * 8/2007 Liu ..... H01S 3/1112 372/30
2009/0231682 A1 9/2009 Kashyap et al. ... G02B 6/02095 359/341.1
2009/0297108 A1 12/2009 Ushiwata et al.
2010/0098112 A1 * 4/2010 Gapontsev ..... H01S 3/0675 372/3
2011/0091155 A1 4/2011 Yilmaz et al.
2012/0300797 A1 * 11/2012 Durkin ..... H01S 5/4006 372/6
2013/0272657 A1 10/2013 Salokatve
2016/0111851 A1 4/2016 Kliner et al.

OTHER PUBLICATIONS

Wetter et al., "High power cladding light strippers," Proc. of SPIE, 6873:687327-1-687327-8 (Jan. 21, 2008).

* cited by examiner

SLANTED FBG FOR SRS SUPPRESSION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[CROSS REFERENCE] *CROSS-REFERENCE* TO RELATED [APPLICATION] *APPLICATIONS*

This application *is a reissue application of U.S. Pat. No. 9,634,462, issued Apr. 25, 2017, which* claims the benefit of U.S. Provisional Patent Application No. 62/064,371, entitled SLANTED FBG FOR SRS SUPPRESSION, filed on Oct. 15, 2014, *both of* which [is] *are* incorporated by reference herein.

FIELD

The field of the disclosed technology is generally fiber lasers and fiber amplifiers that can generate Stimulated Raman Scattering.

BACKGROUND

The maximum power of a CW or pulsed fiber source is ultimately limited by the onset of nonlinear processes in the optical fiber, such as Stimulated Raman Scattering (SRS), Stimulated Brillouin Scattering (SBS), self-phase modulation (SPM), four-wave mixing (4WM), etc. Such non-linear processes generally set a power ceiling for conventional continuous-wave lasers producing multiple kW of output power and pulsed laser sources in beams having high beam quality (e.g., single-mode, few-mode). As optical powers increase, Stimulated Raman scattering (SRS) is one of the most significant nonlinear processes establishing this ceiling. Suppression of SRS is thus desirable for power scaling of fiber lasers and amplifiers.

SUMMARY

In some examples of the disclosed technology, apparatuses can comprise an optical fiber that includes a core and cladding, the core being situated to propagate an optical beam along a propagation axis associated with the core; and at least one fiber Bragg grating (FBG) situated in the core of the optical fiber, the fiber Bragg grating including a plurality of periodically spaced grating portions situated with respect to the propagation axis so that light associated with Raman scattering is directed out of the core so as to reduce the generation of optical gain associated with stimulated Raman scattering (SRS).

In additional examples of the disclosed technology, apparatuses can comprise a gain fiber that includes an actively doped core defining a propagation axis and a pump cladding surrounding the actively doped core, the gain fiber being situated to generate a signal beam; one or more pump sources optically coupled to the gain fiber to provide pump light for generation of the signal beam; a high reflector fiber Bragg grating (FBG) optically coupled to an end of the gain fiber active core and situated to reflect the signal beam propagating in the active core of the gain fiber; a partial reflector FBG optically coupled to an opposite end of the gain fiber active core and situated to partially reflect the signal beam and to transmit an output beam; and at least one slanted stimulated Raman scattering (SRS) FBG situated in the gain fiber so as to direct light associated with Raman scattering out of the gain fiber so as to reduce the generation of optical gain associated with SRS in the gain fiber.

In further examples of the disclosed technology, apparatuses can comprise an optical fiber that includes a core and cladding, the core being situated to propagate an optical beam along a propagation axis associated with the core; and at least one spectrally selective component optically coupled to the core of the optical fiber, the spectrally selective component including at least one optical redirecting portion situated at a non-perpendicular angle with respect to the propagation axis so that light associated with Raman scattering is directed out of the core so as to reduce the generation of optical gain associated with stimulated Raman scattering (SRS).

The foregoing and other objects, features, and advantages of the invention will become more apparent from the following detailed description, which proceeds with reference to the accompanying figures.

DETAILED DESCRIPTION

Figure 1:
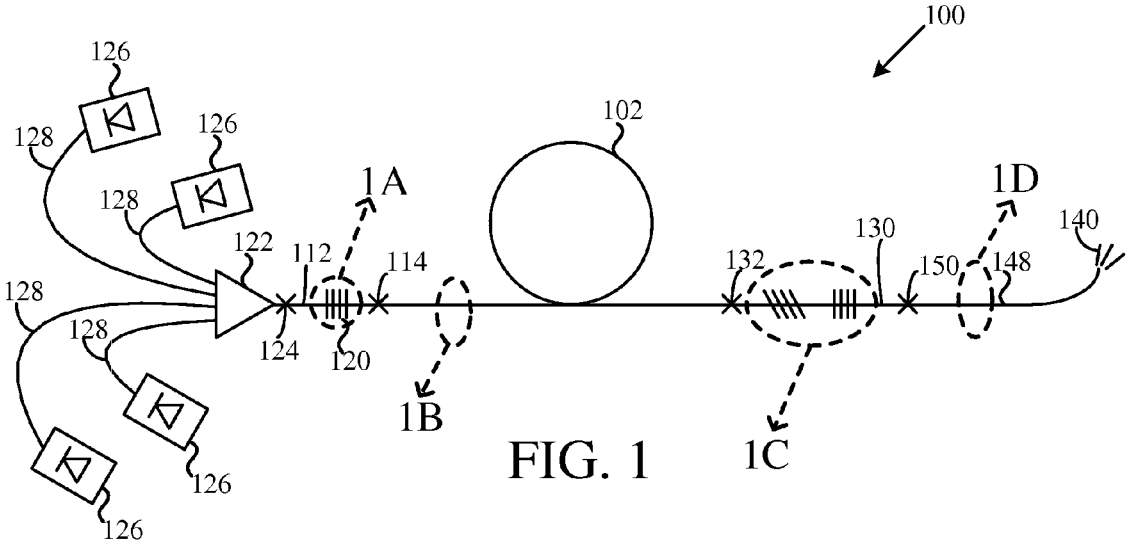
FIG. 1 is a schematic of an embodiment of a fiber laser.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections. Examples may be described with reference to directions indicated as "above," "below," "upper," "lower," and the like. These terms are used for convenient description, but do not imply any particular spatial orientation unless the context clearly indicates a particular orientation.

As used herein, optical radiation refers to electromagnetic radiation at wavelengths of between about 100 nm and 10 μm, and typically between about 500 nm and 2 μm. Examples based on available laser diode sources and optical fibers generally are associated with wavelengths of between about 800 nm and 1700 nm. In some examples, propagating optical radiation is referred to as one or more beams having diameters, asymmetric fast and slow axes, beam cross-sectional areas, and beam divergences that can depend on beam wavelength and the optical systems used for beam shaping. For convenience, optical radiation is referred to as light in some examples, and need not be at visible wavelengths.

Representative embodiments are described with reference to optical fibers, but other types of optical waveguides can be used having square, rectangular, polygonal, oval, elliptical or other cross-sections. Optical fibers are typically formed of silica (glass) that is doped (or undoped) so as to provide predetermined refractive indices or refractive index differences. In some, examples, fibers or other waveguides are made of other materials such as fluorozirconates, fluoroaluminates, fluoride or phosphate glasses, chalcogenide glasses, or crystalline materials such as sapphire, depending on wavelengths of interest. Refractive indices of silica and fluoride glasses are typically about 1.5, but refractive indices of other materials such as chalcogenides can be 3 or more. In still other examples, optical fibers can be formed in part of plastics. In typical examples, a doped waveguide core such as a fiber core provides optical gain in response to pumping, and core and claddings are approximately concentric. In other examples, one or more of the core and claddings are decentered, and in some examples, core and cladding orientation and/or displacement vary along a waveguide length.

As used herein, numerical aperture (NA) refers to a largest angle of incidence with respect to a propagation axis defined by an optical waveguide for which propagating optical radiation is substantially confined. In optical fibers, fiber cores and fiber claddings can have associated NAs, typically defined by refractive index differences between a core and cladding layer, or adjacent cladding layers, respectively. While optical radiation propagating at such NAs is generally well confined, associated electromagnetic fields such as evanescent fields typically extend into an adjacent cladding layer. In some examples, a core NA is associated with a core/inner cladding refractive index, and a cladding NA is associated with an inner cladding/outer cladding refractive index difference. For an optical fiber having a core refractive index $n_{core}$ and a cladding index $n_{clad}$, a fiber core NA is $NA=\sqrt{n_{core}^2-n_{clad}^2}$. For an optical fiber with an inner core and an outer core adjacent the inner core, a cladding NA is $NA=\sqrt{n_{inner}^2-n_{outer}^2}$, wherein $n_{inner}$ and $n_{outer}$ are refractive indices of the inner cladding and the outer cladding, respectively. Optical beams as discussed above can also be referred to as having a beam NA which is associated with a beam angular radius. While multi-core step index fibers are described below, gradient index designs can also be used.

In the examples disclosed herein, a waveguide core such as an optical fiber core is doped with a rare earth element such as Nd, Yb, Ho, Er, or other active dopants or combinations thereof. Such actively doped cores can provide optical gain in response to optical or other pumping. As disclosed below, waveguides having such active dopants can be used to form optical amplifiers, or, if provided with suitable optical feedback such as reflective layers, mirrors, Bragg gratings, or other feedback mechanisms, such waveguides can generate laser emissions. Optical pump radiation can be arranged to co-propagate and/or counter-propagate in the waveguide with respect to a propagation direction of an emitted laser beam or an amplified beam.

The term brightness is used herein to refer to optical beam power per unit area per solid angle. In some examples, optical beam power is provided with one or more laser diodes that produce beams whose solid angles are proportional to beam wavelength and beam area. Selection of beam area and beam solid angle can produce pump beams that couple selected pump beam powers into one or more core or cladding layers of double, triple, or other multi-clad optical fibers.

Fiber Bragg gratings are described herein as one or more Bragg grating that are "written" into optical fibers to produce a refractive index variation associated with a Bragg reflection. Fiber Bragg gratings can be written in optical fibers in a variety of ways to produce the corresponding refractive index variation, including during or after the fabrication of the optical fiber in which the FBG is to be written. The photosensitivity of an optical fiber generally allows the refractive index to be changed by an incident optical beam provided with suitable characteristics (wavelength, intensity, pulse duration, etc.) provided the fiber also has suitable composition characteristics. In typical examples, FBGs are written into lengths of active or passive optical fiber cores with pulsed lasers, such as excimer or femtosecond sources, situated to selectively irradiate the core in a spatially periodic pattern to produce a refractive index variation, or modulation, in the core corresponding to a desired reflectivity spectrum.

Stimulated Raman scattering (SRS) typically transfers light propagating in a fiber core from a signal wavelength to a longer wavelength, known as Stokes shifts, or shorter wavelengths, known as anti-Stokes shifts. As will be discussed further herein, introducing a wavelength-dependent distributed loss in a fiber allows SRS to be suppressed without causing loss of the signal beam, thereby preventing SRS buildup and allowing power scaling at the signal wavelength. Such a distributed loss can be provided by one or more fiber Bragg gratings (FBG) written at one or more locations along the fiber. The FBG is angled so as to reject light at the SRS wavelength from the fiber core. The rejected light can be directed out of the core and into the cladding or out of the cladding. Examples discussed herein can be implemented in fiber lasers or fiber amplifiers, including broadband continuous-wave systems, short-pulsed systems (e.g., less than 1 ns), quasi-continuous-wave systems, etc.

In some examples, FBGs can be written with the grating being tilted with respect to the fiber beam propagation axis. Design parameters for the FBGs include the grating angle, the length of the grating, the depth of the grating (e.g., the amplitude of the index modulation), whether the FBG is located along the entire fiber or at specific locations, and whether the FBG has a uniform period or is made non-uniform (e.g., to broaden its spectral bandwidth or otherwise influence its reflectivity). In some examples, such as with multimode fibers, multiple FBG patterns can be overwritten on the same location so as to address different modes, wavelength, polarizations, or other beam properties. FBGs written at different locations can also have different patterns. The one or more FBGs cause SRS light to be directed out of the fiber through conduction, dissipation, optical processes, or combinations thereof. In some examples, the FBG can be written along the entire length of the active optical fiber. In other examples, the FBG is written along only a portion of the active optical fiber. Various features of the examples herein can also be applied to other examples herein.

Figure 1A:
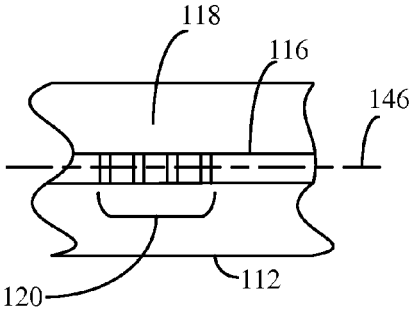
FIGS. 1A-D are exploded cross-sectional views of selected portions of fiber lengths of the fiber laser in FIG. 1.
Figure 1B:
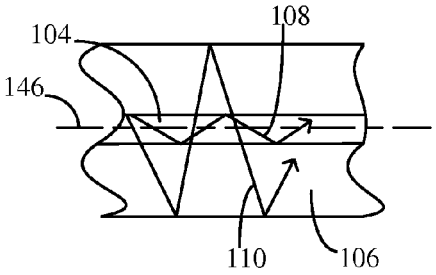

Referring to FIG. 1 and corresponding exploded views FIGS. 1A-1D, a fiber laser 100 includes an active fiber 102 that includes a core 104 and cladding 106 surrounding the core 104 (as best seen in FIG. 1B). The core 104 is situated to propagate a signal beam 108 and the cladding 106 is situated to propagate a pump beam 110. The core 104 of the active fiber 102 typically includes one or more active dopants that can be excited by the pump beam 110 as the pump beam 110 propagates through the core 104 to allow laser amplification of the signal beam 108.

A passive fiber section 112 is fiber-spliced to one end of the active fiber 102 at a splice 114. As best seen in FIG. 1A, the passive fiber section 112 includes passive core 116 and a cladding 118 surrounding the passive core 116 each having a similar diameter to the core 104 and cladding 106 of the active fiber 102. In some examples, adjacent or adjoining fiber sections, such as the active fiber 102 and the passive fiber section 112, can have cores and claddings of dissimilar diameter, geometry, or other fiber parameters.

The passive fiber section 112 also includes an HR FBG 120 written into the passive core 116 that is highly reflective at the wavelength (or range) of the signal beam 108 and that is transmissive at the wavelength (or range) of the pump beam 110. A fiber-based pump combiner 122 is spliced to the passive fiber section 112 at a splice 124 and includes a plurality of pump sources 126 coupled to corresponding pump fiber inputs 128. The pump sources 126 produce light at the wavelength of the pump beam 110 and are combined with the fiber-based pump combiner 122 for coupling into the cladding 118 of the passive fiber section 112.

Figure 1C:
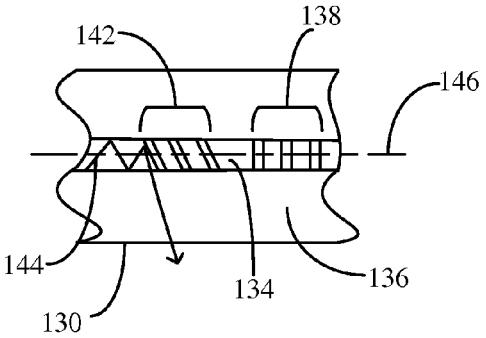
Figure 1D:
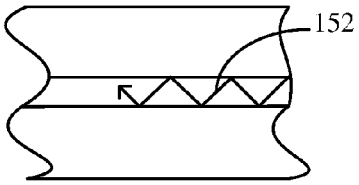

Another passive fiber section 130 is fiber-spliced to the other end of the active fiber 102 at a splice 132. As best seen in FIG. 1C, the passive fiber section 130 includes a passive core 134 and cladding 136 that are generally aligned at the splice 132 with the core and cladding 104, 106 of the active fiber 102 in order to receive the signal beam 108 with minimal loss. The passive fiber section 130 includes a PR FBG 138 written into the passive core 134 and that is partially reflective at the wavelength of the signal beam 108 so as to allow a portion of the signal beam 108 to propagate past the PR FBG 138 to form an output beam 140.

The passive fiber section 130 also includes a SRS FBG 142 written into the passive core 134 with a selected refractive index pitch so that the SRS FBG 142 is highly reflective, or otherwise produces a scattering or optical redirecting effect, at a wavelength range of a first Stokes shift from the signal beam 108 that is associated with Raman scattering. During laser operation, the large power density of the signal beam 108 tends to surpass various nonlinear thresholds and to be associated with the generation of an SRS beam 144 that can cause various deleterious effects, including degradation of one or more components of the fiber laser 100 and ultimately failure of the fiber laser 100. The SRS FBG 142 is situated in the passive core 134 to receive the SRS beam 144 as it is generated and to direct the SRS beam 144 out of the passive core 134. In typical examples, the SRS FBG 142 includes one or more refractive index varied portions that are arranged at a non-perpendicular angle with respect to a propagation axis 146 of SRS beam 144 in the passive core 134. In further examples, the SRS FBG 142 can be replaced with another spectrally selective component, such as a fused wavelength-division multiplexer type coupler or a micro-optic based spectral filter. Spectrally selective components can be situated in-line with the passive fiber section 130 and some examples can include controlled free-space propagation and in-spectral filtering of the free-space beam.

In the architecture of the fiber laser 100 shown in FIG. 1, a peak power density for the signal beam 108 typically occurs in proximity to the PR FBG 138. Thus, situating the SRS FBG 142 adjacent to the PR FBG 138 towards the active fiber 102 allows the FBGs 138, 142 to be written successively in the same passive fiber section 130, thereby increasing manufacturing efficiency, and to increase attenuation of the SRS beam 144 as it is being generated in the fiber laser 100. By inhibiting generation of the SRS beam 144 through selective attenuation in the oscillator, e.g., the core volume situated between the HR and PR FBGs 120, 138, of the fiber laser 100, other components of the fiber laser 100, such as the pump sources 126, the fiber-based pump combiner 122, and the active fiber 102, can be protected from damage associated with SRS.

A delivery fiber 148 is spliced to the passive fiber section 130 at a splice 150 and provides a propagation path out of the fiber laser 100 for the output beam 140. The SRS FBG 142 is also situated to receive a residual SRS beam 152 (shown in FIG. 1D) that is emitted from the delivery fiber 148, reflected from a processing target (now shown), and coupled back into the delivery fiber 148 and passive core 134. The SRS FBG 142 also directs the residual SRS beam 152 out of the passive core 134 to remove the residual SRS beam 152 from the fiber laser 100. By removing the residual SRS beam 152, additional SRS gain in the fiber laser 100 associated with the SRS beam 144 is reduced or eliminated, further protecting the fiber laser 100 and its components.

Figure 2:
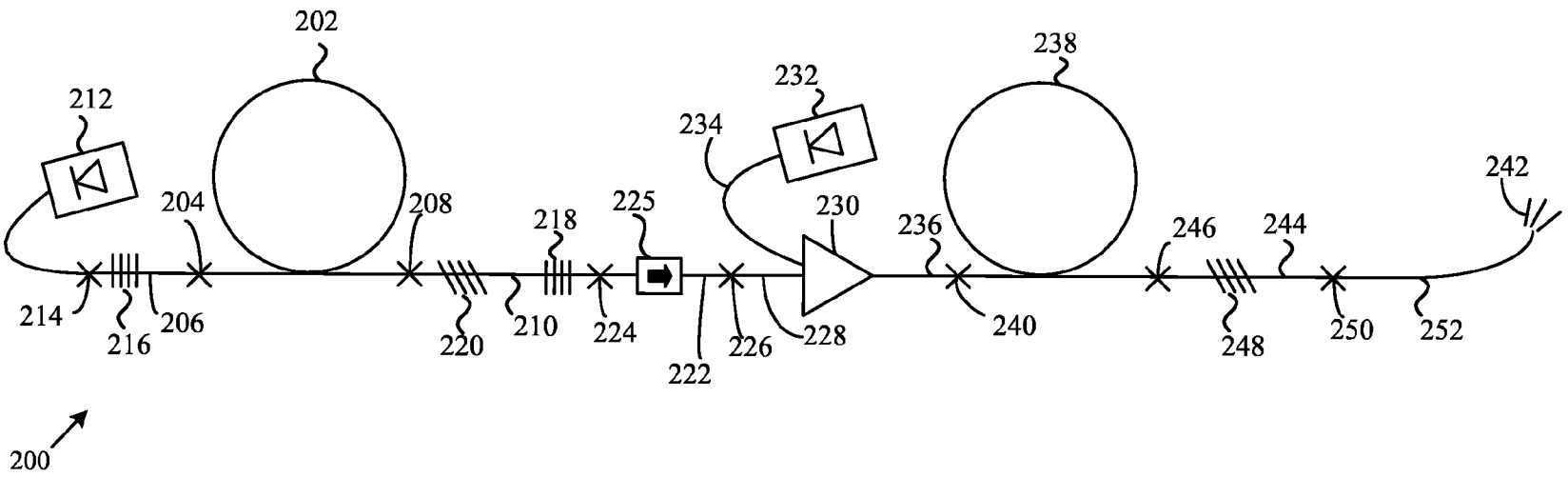
FIG. 2 is a schematic of another embodiment of a fiber laser.

In FIG. 2 a fiber laser 200 is shown in a master-oscillator power-amplifier architecture. The fiber laser 200 includes an active oscillator fiber 202 optically coupled with an optical splice 204 at a first end to a passive fiber section 206 and optically coupled with an optical splice 208 at a second end to another passive fiber section 210. The active oscillator fiber 202 includes a core and cladding and generates a signal beam in the core. One or more fiber-coupled pump sources 212 is optically coupled to the passive fiber section 206 with an optical splice 214. The fiber-coupled pump source 212 delivers a pump beam to the active oscillator fiber 202 so that the signal beam can be generated in the core of the active oscillator fiber 202. The passive fiber section 206 includes an FBG 216 in the core of the passive fiber section 206 that is highly reflective at the wavelength of the signal beam so that the signal beam generated in the core of the active oscillator fiber 202 and propagating towards the FBG 216 is substantially reflected by the FBG 216. The passive fiber section 210 includes an FBG 218 that is partially reflective at the wavelength of the signal beam to allow a portion of the signal beam to propagate past the FBG 218. The passive fiber section 210 also includes an FBG 220 that includes refractive index variation features that generally form a non-perpendicular angle with respect to a propagation axis of the signal beam in the core of the passive fiber section 206. The FBG 220 is situated to couple out an SRS beam that propagates in the core of the active oscillator fiber 202 and the passive fiber sections 206, 210 as the SRS beam is being generated so as to reduce the destructive effects associated with Raman gain or other nonlinear effects.

A passive fiber section 222 is spliced at a splice 224 to an emitting end of the passive fiber section 210 and receives the portion of the signal beam allowed to propagate past the FBG 218. The passive fiber section 222 includes an optical isolator 225 that is situated to extract amplified spontaneous emission (ASE) or other optical noise associated with the signal beam. The passive fiber section 222 is fiber spliced via splice 226 to a passive fiber input 228 of a pump combiner 230 that is all-glass. One or more fiber-coupled pump sources 232 are also coupled to the pump combiner 230 via fiber inputs 234. A passive fiber section output 236 of the pump combiner 230 delivers the signal beam from the passive fiber section 222 and the pump beam from the pump source 232 to an active amplifier fiber 238 via an optical splice 240. As the signal beam propagates in the core of the active amplifier fiber 238, it increases in power to form an output beam 242 that is emitted from the fiber laser 200. A passive fiber section 244 is optically coupled with an optical splice 246 to the active amplifier fiber 238 and includes an FBG 248 situated in the core of the passive fiber section 244 at a non-perpendicular angle with respect to the propagating signal beam. The FBG 248 couples out SRS light propagating in the core so as to inhibit the generation of SRS and to reduce the damaging effects associated with SRS. The passive fiber section 244 is also spliced at a splice 250 to a delivery fiber 252 that is situated to receive the output beam 242 with a reduced amount of SRS light.

Figure 3:
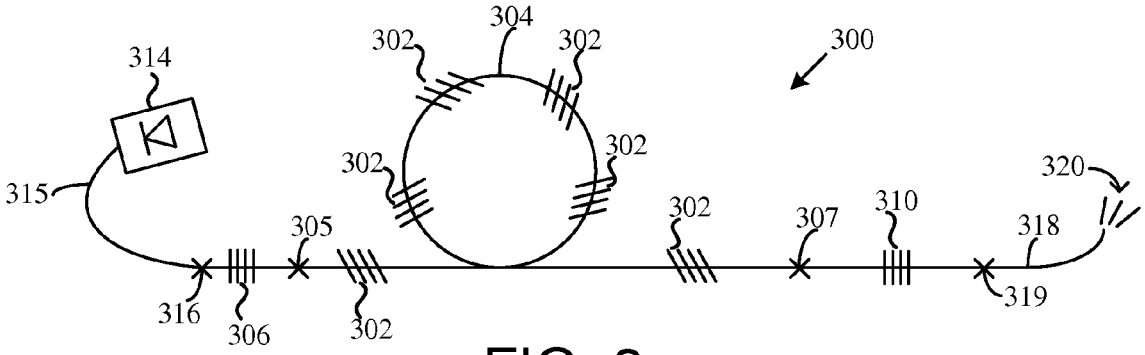
FIGS. 3-5 are schematics of portions of different fiber laser embodiments.

FIG. 3 shows an example of a fiber laser 300 that includes a plurality of SRS FBGs 302 written into a core of an active gain fiber 304 at selected positions along the length of the active gain fiber 304. The fiber laser 300 can include components similar to fiber laser 100, including an HR FBG 306 situated in a core of a passive fiber length 308 spliced to the active gain fiber 304 at a splice 305, a PR FBG 310 situated in a core of a passive fiber length 312 spliced to the active gain fiber 304 at a splice 307, a pump source 314 coupled to a pump fiber 315 that is coupled to the passive fiber length 308 with a splice 316, and a delivery fiber 318 coupled to the passive fiber length 312 at a splice 319. The HR and PR FBGs 306, 310 form an oscillator with the gain medium provided by the core of the active gain fiber 304. An output beam 320 is emitted from an end of a delivery fiber 318 that can be used for various material processes as well as for other lasers (such as for pumping another laser or combining into a more powerful beam).

As Raman scattering occurs that is associated with the amplification of a signal beam in the core of the active gain fiber, SRS can occur and increase in gain competing with the signal beam and transferring energy from the signal beam. The SRS FBGs 302, which can generally be situated at a non-perpendicular angle with respect to the core of the active gain fiber 304, are distributed along the length of active gain fiber 304 so as to introduce a distributed SRS loss that inhibits the generation of SRS along the length of the active gain fiber 304. In general, the pitch of the refractive index variation associated with the SRS FBGs 302 situated in the active gain fiber 304 can be different from the pitch of an SRS FBG situated in a passive fiber section, due to dissimilarities in material composition between the active and passive core. The output beam 320 thus has a reduced SRS power content as compared with beams of conventional lasers.

Figure 4:
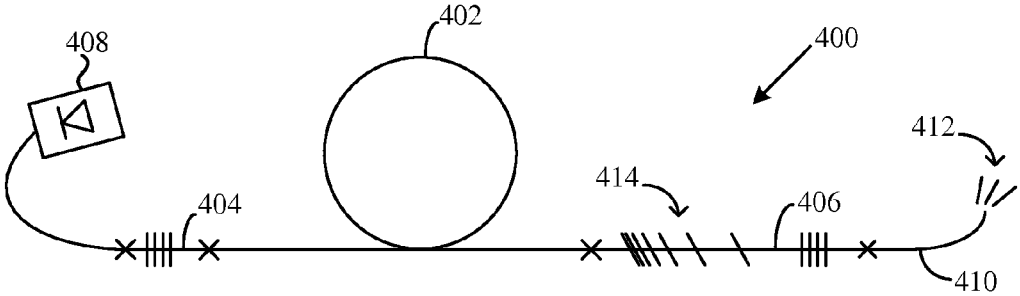

In FIG. 4, another example of a fiber laser 400 is shown that is directed to suppression of SRS. The fiber laser 400 includes an active gain fiber 402 coupled to opposite passive fiber sections 404, 406, one or more pump sources 408 coupled to the passive fiber section 404, and a delivery fiber 410 coupled to the passive fiber section 406 for receiving and delivering a high power output beam 412. An FBG 414 is written into the core of the passive fiber section 406 at a chirped periodicity. For example, the period of the refractive index variation provided in the core by the FBG 414 varies along length of the core, such as with sequentially increasing distances. In some examples, the periodicity is varied to expand the reflectivity spectrum so as to extend over the wavelength (or range) associated with SRS of the output beam 412. The FBG 414 is also angled with respect to the propagation path of the output beam 412 in order couple the SRS light out of the core of the fiber laser 400.

Figure 5:
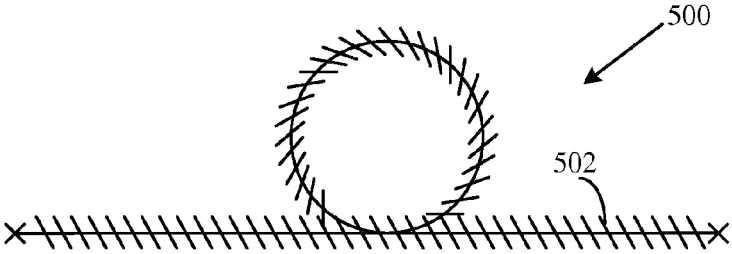

FIG. 5 shows an example of a fiber 500 with an active core that includes FBG portions 502 substantially distributed along the length of the fiber 500. In various examples, the FBG portions 502 can be evenly spaced from one another as well with variable spacing. The FBG portions 502 introduce very low loss for pump light and signal light propagating in the core but introduce significant loss at Raman wavelengths associated with the signal light so that SRS is inhibited during active laser operation. Each FBG portion 502 can include one or more refractive index varied portions. The cumulative effect of the FBG portions 502 distributed along the fiber 500 acts to reduce the growth of SRS in a fiber laser in which the fiber 500 is situated. The FBG portions 502 can be similar to the plurality of FBGs 302 in the fiber laser 300, though the FBG portions 502 generally include fewer refractive index varied portions than the FBGs 302 (e.g., a single dip and rise or rise and dip in refractive index may suffice) or the spacing between adjacent FBG portions 502 is closer, or both.

Figure 6:
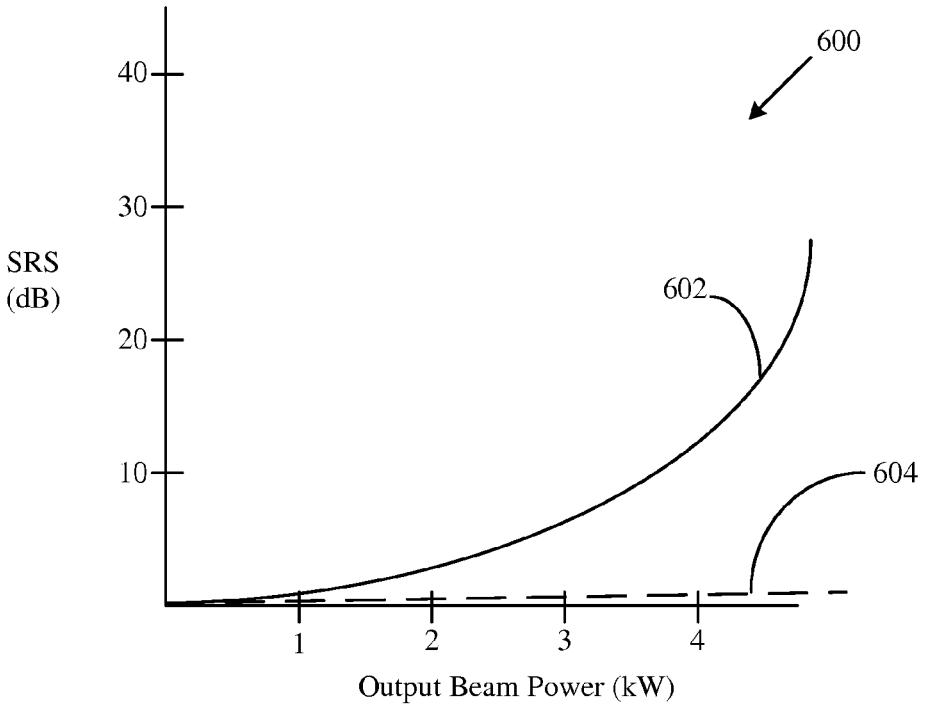
FIG. 6 is a chart of SRS beam power versus output beam power.

FIG. 6 is a plot 600 depicting SRS gain in a fiber laser as a function of the output beam power of the fiber laser. Referring to line 602, in a conventional fiber laser, SRS generally increases as the continuous-wave power of the fiber laser rises into the kW regime, leading to detrimental effects within the fiber laser and to the characteristics of the output beam of the fiber laser. Line 604 shows predicted SRS performance in accordance with examples of the disclosed technology. As the continuous-wave output beam power of the fiber laser increases and the threshold for SRS generation associated with the output beam is passed, SRS gain is maintained at a minimum with FBG-based loss components introduced into the fiber laser system inhibiting the generation of SRS.

Figure 7:
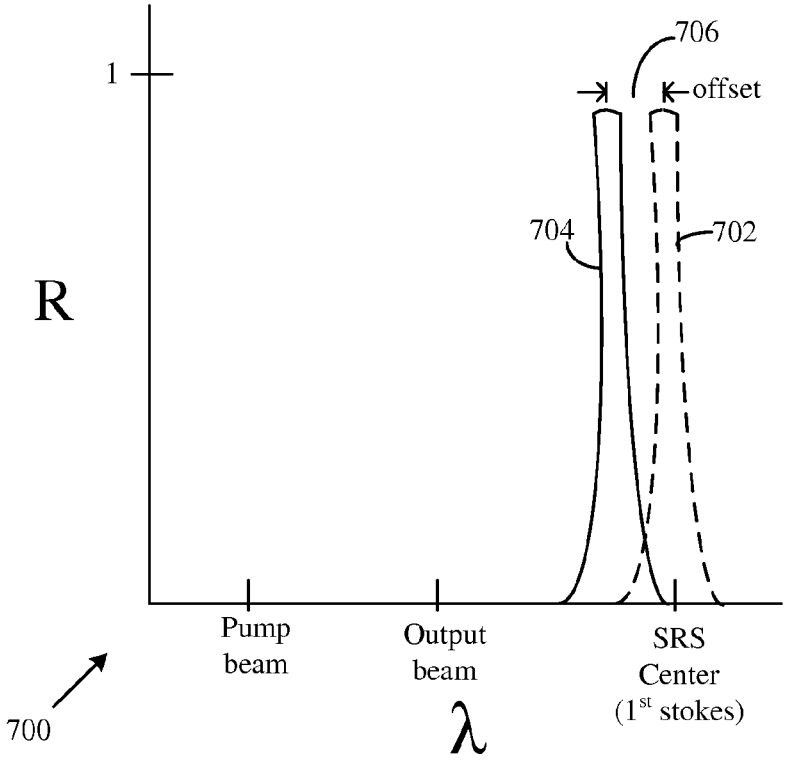
FIG. 7 is a chart of FBG reflectivity versus wavelength.

FIG. 7 shows a plot 700 of FBG reflectivity with respect to optical wavelength. In typical examples herein, the reflectivity characteristics of an FBG used to inhibit generation of SRS are selected to coincide with an SRS wavelength associated with an output beam. For example, a reflectivity spectrum 702 generally coincides with a center wavelength of a first Stokes shift from an output beam wavelength (e.g., 1080 nm) of a fiber laser. In additional examples, a reflectivity spectrum 704 is selected with a spectral offset 706 shifting the reflectivity spectrum 704 in relation to a desired reflectivity spectrum 702. In different examples herein, SRS-related FBGs can be situated in proximity to heat loads of different magnitude resulting in different localized temperatures. For higher temperatures, one or more FBGs situated to introduce SRS loss can have a reflectivity spectrum that is offset so that as temperature of the FBG increases during normal fiber laser operation, the corresponding reflectivity spectrum shifts to coincide with an SRS wavelength. For example, spectral offsets can include between 0.01 and 0.1 nm, 0.1 nm and 1.0 nm, 1 nm and 10 nm, or greater. Separate SRS-related FBGs can be situated in a fiber laser and have different spectral offsets to correspond with the temperature associated with the region in which the FBGs are situated. Moreover, a plurality of SRS-related FBGs can have different offsets (or no offsets) to ensure that variation in temperature does not affect the ability to maintain SRS suppression.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope and spirit of the appended claims.

We claim:

1. An apparatus, comprising:

an optical fiber including a core and cladding, the core being situated to propagate an optical beam along a propagation axis associated with the core; and at least one fiber Bragg grating (FBG) situated in the core of the optical fiber, the fiber Bragg grating including a plurality of periodically spaced grating portions situated with respect to the propagation axis so that light associated with Raman scattering is directed out of the core *and cladding* so as to reduce the generation of optical gain associated with stimulated Raman scattering (SRS);

wherein the FBG defines a reflection bandwidth that is offset from a center wavelength of a first Raman Stokes wavelength range of the optical beam[so as to compensate for a shift of the reflection bandwidth associated with localized heating of the FBG from the propagation of the optical beam].

2. The apparatus of claim 1, wherein the plurality of periodically spaced grating portions are situated at a non-perpendicular angle with respect to the propagation axis.

3. The apparatus of claim 1, wherein the at least one FBG is situated within a fiber oscillator defined between a high-reflecting FBG and a partially-reflecting FBG.

4. The apparatus of claim 3, wherein the at least one FBG is situated adjacent to the partially-reflecting FBG.

5. The apparatus of claim 4, wherein the at least one FBG and the partially-reflecting FBG are situated in a passive section of optical fiber that is spliced to an active fiber of the fiber oscillator.

6. The apparatus of claim 1, wherein the at least one FBG comprises a plurality of FBGs spaced apart from each other and distributed along the length of the optical fiber.

7. The apparatus of claim 6, wherein the optical fiber includes an active core and the plurality of FBGs are spaced apart along the length to produce a distributed SRS loss in the optical fiber.

8. The apparatus of claim 6, wherein each FBG of the plurality of FBGs includes a single refractive index varied portion.

9. The apparatus of claim 1, wherein the at least one FBG is chirped.

10. The apparatus of claim 1, wherein the offset is between about 0.01 nm and 10 nm.

11. An apparatus, comprising:

a gain fiber including an actively doped core defining a propagation axis and a pump cladding surrounding the actively doped core, the gain fiber being situated to generate a signal beam;

one or more pump sources optically coupled to the gain fiber to provide pump light for generation of the signal beam;

a high reflector fiber Bragg grating (FBG) optically coupled to an end of the gain fiber active core and situated to reflect the signal beam propagating in the active core of the gain fiber;

a partial reflector FBG optically coupled to an opposite end of the gain fiber active core and situated to partially reflect the signal beam and to transmit an output beam; and at least one slanted stimulated Raman scattering (SRS) FBG situated in the gain fiber so as to direct light associated with Raman scattering out of the gain fiber so as to reduce the generation of optical gain associated with SRS in the gain fiber;

wherein the at least one slanted SRS FBG defines a reflection bandwidth that is offset from a center wavelength of a first Raman Stokes wavelength range of the signal beam[so as to compensate for a shift of the reflection bandwidth associated with localized heating of the at least one slanted SRS FBG from the propagation of the signal beam].

12. The apparatus of claim 11, wherein the at least one slanted SRS FBG includes a first SRS FBG situated in a passive core of a passive fiber section of the gain fiber.

13. The apparatus of claim 12, wherein the first SRS FBG is situated between the actively doped core of the gain fiber and the partial reflector FBG.

14. The apparatus of claim 11, wherein the output beam is single-mode or multi-mode.

15. The apparatus of claim 11, wherein the gain fiber is an oscillator fiber and the apparatus further comprises:

an amplifier fiber situated to receive the output beam from the oscillator fiber and to amplify the output beam; and at least another slanted FBG situated in the amplifier fiber so as to direct light associated with Raman scattering out of the amplifier fiber so as to reduce the generation of optical gain associated with SRS in the amplifier fiber.

16. An apparatus, comprising:

an optical fiber including a core and cladding, the core being situated to propagate an optical beam along a propagation axis associated with the core; and

[at least one] *two or more* spectrally selective [component] *components* optically coupled to the core of the optical fiber, the spectrally selective [component] *components* including at least [one] *two* optical redirecting [portion] *portions* situated at [a] non-perpendicular [angle] *angles* with respect to the propagation axis *and including different respective spectrally selective component pitches wherein the non-perpendicular angles and the pitches are selected* so that light associated with Raman scattering is directed out of the core [so as to reduce the generation of optical gain associated with stimulated Raman scattering (SRS)] *and cladding*;

wherein [the] at least one *of the two or more* spectrally selective [component] *components* defines a reflection bandwidth that is offset from a center wavelength of a first Raman Stokes wavelength range of the optical beam[so as to compensate for a shift of the reflection bandwidth associated with heating proximate the at least one spectrally selective component from the propagation of the optical beam].

*17. The apparatus of claim 16, wherein the two or more spectrally selective components are FBGs.*

*18. The apparatus of claim 17, wherein the two optical redirecting portions include slanted elements of the FBG.*

*19. The apparatus of claim 18, wherein the FBG is situated to reduce the generation of optical gain associated with stimulated Raman scattering (SRS).*

*20. The apparatus of claim 16, wherein the offset is configured to compensate for a shift of the reflection bandwidth associated with heating proximate the at least one spectrally selective component from the propagation of the optical beam, and wherein the offset is selected based on an operating temperature proximate the at least one spectrally selective component.*

*21. An apparatus, comprising:*

*an optical fiber including a core and cladding, wherein the core is configured to propagate an optical beam; and*

*a fiber Bragg grating situated in the core, wherein the fiber Bragg grating includes angled reflective elements configured to direct out of the core stimulated Raman scattering (SRS) light associated with the optical beam, wherein the fiber Bragg grating has a first reflectivity spectrum that is offset from and selected to shift to a second reflectivity spectrum coincident with an SRS wavelength responsive to heat loading.*

*22. The apparatus of claim 21, wherein the offset includes between 0.01 nm and 0.1 nm, between 0.1 nm and 1.0 nm, or between 1 nm and 10 nm.*

*23. The apparatus of claim 21, wherein the optical fiber is a first optical fiber and the fiber Bragg grating is a first fiber Bragg grating, and further comprising:*

*a second fiber Bragg grating situated in the core of the first optical fiber or in a core of a the second optical fiber coupled to the first optical fiber, wherein the second fiber Bragg grating is configured with a reflectivity spectrum offset that is different from the offset of the first fiber Bragg grating.*

*24. The apparatus of claim 23, wherein the offsets of the first and second fiber Bragg gratings are configured to provide SRS suppression over a temperature range.*

*25. The apparatus of claim 1, wherein the light directed out of the core and cladding is directed out of the optical fiber.*

*26. The apparatus of claim 17, wherein at least one of the FBGs is situated in an active fiber portion and at least one of the FBGs is situated in a passive fiber portion.*

*27. The apparatus of claim 23, wherein the offsets are configured in relation to different localized temperatures associated with the regions in which the respective FBGs are situated.*

*28. An apparatus, comprising:*

*an optical fiber including a core and cladding, the core being situated to propagate an optical beam along a propagation axis associated with the core; and*

*at least one fiber Bragg grating (FBG) situated in the core of the optical fiber, the fiber Bragg grating including a plurality of periodically spaced grating portions situated with respect to the propagation axis so that light associated with Raman scattering is directed out of the core so as to reduce the generation of optical gain associated with stimulated Raman scattering (SRS);*

*wherein the at least one FBG comprises a plurality of FBGs spaced apart from each other and distributed along the length of the optical fiber, wherein each of the FBGs of the plurality of FBGs has a single rise and dip or dip and rise of refractive index;*

*wherein the at least one FBG defines a reflection bandwidth that is offset from a center wavelength of a first Raman Stokes wavelength range of the optical beam.*

* * * * *